United States Patent [19]
Hawkins et al.

[11] Patent Number: 5,869,289
[45] Date of Patent: Feb. 9, 1999

[54] HUMAN GALECTIN HOMOLOG

[75] Inventors: Phillip R. Hawkins; Olga Bandman, both of Mountain View, Calif.

[73] Assignee: Incyte Pharmaceuticals, Inc., Palo Alto, Calif.

[21] Appl. No.: 728,521

[22] Filed: Oct. 9, 1996

[51] Int. Cl.[6] ............................ C12N 15/00; C12N 15/63; C12N 15/85; C12Q 1/68
[52] U.S. Cl. ...................... 435/69.1; 435/320.1; 435/325; 435/6; 530/350; 536/24.5; 536/23.5
[58] Field of Search .................... 435/6, 320.1; 536/23.1, 536/24.5

[56] References Cited

FOREIGN PATENT DOCUMENTS

WO 96/21671   7/1996   WIPO .

OTHER PUBLICATIONS

Wagner R, Nature, vol. 372 pp. 333–335, Nov. 24, 1994.
Naeve C et al., Biotechniques, vol. 19, No. 3, pp. 448–453, 1995.
Kroczek R, J. Chrom., vol. 618, pp. 133–145, 1993.
Barondes S et al., Cell, vol.76, pp. 597–598, 1994.
Barondes, S.H. et al., "Structure and Function of a Large Family of Animal Lectins" *J.Biol.Chem.*(1994) 269:20807–20810.
Stoolman, L.M., "Adhesion Molecules Controlling Lymphocyte Migration", *Cell*(1989) 56:907–910.
Abbott, W.M. et al., "Soluble 14–kDa β–Galactoside–specific Bovine Lectin", *J. Biol.Chem.*(1991) 266:5552–5557.
Hirabayashi, J. et al., "Effect of Amino Acid substitution by Site–directed Mutagenesis on the Carbohydrate Recognition and Stability of Human 14–kDa β–Galactoside–binding Lectin", *J. Biol.Chem.* (1991) 35:23648–23653.
Do, K. et al., "Lamp–1 in Cho Cells is a Primary Carrier of Ply–N–Acetyllactosamine Chains and is bound preferentially by a mammalian S–Type Lectin", *Biochem.Biophys. Res.Commun.* (1990) 173:1123–1128.

Skrincosky, D.M. et al., "Galaptin–mediated Adhesion of Human Ovarian Carcinoma A121 Cells and Detection of Cellular Galaptin–binding Glycoproteins", *Cancer Res.* (1993) 53: 2667–2675.
Erratum (1993) *Cancer Res.*(1993) 53:3652.
Gu, M. et al., "Selective modulation of the interaction of αhd 7βhd 1 integrin with fibronectin and laminin by L–14 lectin during skeletal muscle differentiation", *J.Cell Sci.* (1994) 107:175–181.
Mahanthappa, N.K. et al., "Rat olfactory neurons can utilize the endogenous lectin, L–14 in a novel adhesion mechanism", *Development* (1994) 120:1373–1384.
Liu, F., "S–type mammalian lectins in allergic inflammation", *Immunol.Today* (1993) 14:486–490.
Frigeri, L.G. et al., "εBP, a β–Galactoside–Binding Animal Lectin, Recognises IgE Receptor (FcεRI) and activates Mast Cells", *Biochem.*(1993) 32:7644–7649.
Oda, Y. et al., "Soluble Lactose–binding Lectin from Rat Intestine with Two Different Carbohydrate–binding Domains in the Same Peptide Chain", *J.Biol.Chem.* (1993) 268:5929–5939.

(List continued on next page.)

*Primary Examiner*—Eric Grimes
*Assistant Examiner*—Peter P. Tung
*Attorney, Agent, or Firm*—Leanne C. Price; Lucy J. Billings; Incyte Pharmaceuticals, Inc.

[57] ABSTRACT

The present invention provides a polynucleotide which identifies and encodes a novel human galectin-8. The invention provides for genetically engineered expression vectors and host cells comprising the nucleic acid sequence encoding human galectin-8. The invention also provides for the production and use of substantially purified human galectin-8 in pharmaceutical compositions to increase immune responses. The invention also provides for the use of antisense molecules and antibodies in pharmaceutical compositions to decrease immune response. The invention also describes diagnostic assays which utilize the polynucleotide to hybridize with the transcripts and/or genomic DNA encoding human galectin-8 and anti-human galectin-8 antibodies which specifically bind to human galectin-8.

11 Claims, 4 Drawing Sheets

```
  1  M M L S L N N L Q N I I Y N P V I P Y V G T I P D Q L D P G T L I V I C G H V P   305603
  1  M - L S L S N L Q N I I Y N P T I P Y V S T I T E Q L K P G S L I V I R G H V P   g717032

41  S D A D R F Q V D L Q N G S S V K P R A D V A F H F N P R F K R A G C I V C N T   305603
 40  K D S E R F Q V D F Q H G N S L K P R A D V A F H F N P R F K R S N C I V C N T   g717032

81  L I N E K W G R E E I T Y D T P F K R R K S F E I V I M V L K D K F Q - - - - -   305603
 80  L T N E K W G W E E I T H D M P F R K E K S F E I V I M V L K N K F H V A V N G   g717032

116  - - - - - - - - - - - - - - - - - - - - - - - - - - - D L Q S T                 305603
120  K H I L L Y A H R I N P E K I D T L G I F G K V N I H S I G F R F S S D L Q S M   g717032

121  Q A S S L E L T E I S R E N V P K S G T X Q L C L P F X A R L N T P M G P G R T   305603
160  E T S T L G L T Q I S K E N I Q K S G K L H L S L P F E A R L N A S M G P G R T   g717032

161  V V V K G E V N A N A K S F N V D L L A G K S K D I A L H L N P R L N I K A F V   305603
200  V V V K G E V N T N A T S F N V D L V A G R S R D I A L H L N P R L N V K A F V   g717032

201  R N S F L Q E S W G E E E R N I T S F P F S P G M Y F E M I I Y C D V R E F K V   305603
240  R N S F L Q D A W G E E E R N I T C F P F S S G M Y F E M I I Y C D V R E F K V   g717032

241  A V N G V H S L E Y K H R F K E L X S I S A X N                                   305603
280  A V N G V H S L E Y K H R F K D L S S I D T L A V D G D I R L L D V R S W        g717032
```

OTHER PUBLICATIONS

Magnaldo, T. et al., "Galectin–7, a Human 14–kDa S–Lectin, Specfically Expressed in Keratinocytes and Sensitive to Retinoic Acid", *Develop.Biol.* (1995) 168:259–271.

Madsen, P. et al., "Cloning, Expression, and Chromosome Mapping of Human Galectin–7", *J.Biol.Chem.* (1995) 270:5823–5829.

Hadari, Y.R., et al., "Galectin–8 ", (1995) 270:3447–3453.

Raz, A. et al., "Endogenous galactoside–binding lectins:a new class of functional tumor cell surface molecules related to metastasis", *Cancer Metastasis Rev.* (1987) 6:433–452.

Raz, A. et al., "Differential Expression of Endogenous Lectins on the Surface of Nontumorigenic, tumorigenic, and Metastatic Cells", *Cancer Res.* (1986) 46:3667–3672.

Raz, A. et al., "Evidence for the Role of 34–kDa Galactoside–Binding Lectin in Transformation and metastasis", *Int.J.Cancer* (1990) 46:871–877.

Lobsanov, Y.D. et al., "X–ray Crystal Structure of the Human Dimeric S–Lac Lectin, L–14–II, in complex with Lactose at 2.9–Å Resolution", *J.Biol.Chem.* (1993) 268:27034–27034–27038.

Hirabayashi, J. et al., "Evidence That *caenorhabditis elegans* 32–dDa β–Galactoside–binding Protein is Homologous to vertebrate βGalactoside–binding Lectins", *J.Biol.Chem.*(1992) 267: 15485–15490.

Stites, D.P. et al., "Basic & Clinical Immunology", Lange Medical Publications, Los Altos, CA, (1984) p.100.

Gaudin, J. et al., "Cloning of the cDNA encoding rabbit galectin–3", *Gene.* (1995) 163:249–252.

```
                9                18                27                36                45                54
5' NNT CCC AGG TTC AAG CAA TTG TCC TGT CTC AGC CTC CTG AGT AGC TGG GAC TAC 63                72                81                90                99               108
  AGG GCC AGT GCC TCA GTT TCA ATC CAG GTA ACC TTT AAA TGA AAC TTG CCT AAA 117               126               135               144               153               162
  ATC TTA GGT CAT ACA CAG AAG AGA CTC CAA TCG ACA AGA AGC TGG AAA AGA ATG
                                                                          M 171               180               189               198               207               216
  ATG TTG TCC TTA AAC AAC CTA CAG AAT ATC ATC TAT AAC CCG GTA ATC CCG TAT
   M   L   S   L   N   N   L   Q   N   I   I   Y   N   P   V   I   P   Y 225               234               243               252               261               270
  GTT GGC ACC ATT CCC GAT CAG CTG GAT CCT GGA ACT TTG ATT GTG ATA TGT GGG
   V   G   T   I   P   D   Q   L   D   P   G   T   L   I   V   I   C   G 279               288               297               306               315               324
  CAT GTT CCT AGT GAC GCA GAC AGA TTC CAG GTG GAT CTG CAG AAT GGC AGC AGT
   H   V   P   S   D   A   D   R   F   Q   V   D   L   Q   N   G   S   S 333               342               351               360               369               378
  GTG AAA CCT CGA GCC GAT GTG GCC TTT CAT TTC AAC CCT CGT TTC AAA AGG GCC
   V   K   P   R   A   D   V   A   F   H   F   N   P   R   F   K   R   A 387               396               405               414               423               432
  GGC TGC ATT GTT TGC AAT ACT TTG ATA AAT GAA AAA TGG GGA CGG GAA GAG ATC
   G   C   I   V   C   N   T   L   I   N   E   K   W   G   R   E   E   I 441               450               459               468               477               486
  ACC TAT GAC ACG CCT TTC AAA AGA AGA AAA TCT TTT GAG ATC GTG ATT ATG GTG
   T   Y   D   T   P   F   K   R   R   K   S   F   E   I   V   I   M   V 495               504               513               522               531               540
  CTA AAG GAC AAA TTC CAG GAC TTA CAA AGT ACC CAA GCA TCT AGT CTG GAA CTG
   L   K   D   K   F   Q   D   L   Q   S   T   Q   A   S   S   L   E   L 549               558               567               576               585               594
  ACA GAG ATA AGT AGA GAA AAT GTT CCA AAG TCT GGC ACG NCC CAG CTT TGC CTG
   T   E   I   S   R   E   N   V   P   K   S   G   T   X   Q   L   C   L 603               612               621               630               639               648
  CCA TTC GNT GCA AGG TTG AAC ACC CCC ATG GGC CCT GGA CGA ACT GTC GTC GTT
   P   F   X   A   R   L   N   T   P   M   G   P   G   R   T   V   V   V 657               666               675               684               693               702
  AAA GGA GAA GTG AAT GCA AAT GCC AAA AGC TTT AAT GTT GAC CTA CTA GCA GGA
   K   G   E   V   N   A   N   A   K   S   F   N   V   D   L   L   A   G
```

FIGURE 1A

```
         711         720         729         738         747         756
AAA TCA AAG GAT ATT GCT CTA CAC TTG AAC CCA CGC CTG AAT ATT AAA GCA TTT
 K   S   K   D   I   A   L   H   L   N   P   R   L   N   I   K   A   F 765         774         783         792         801         810
GTA AGA AAT TCT TTT CTT CAG GAG TCC TGG GGA GAA GAA GAG AGA AAT ATT ACC
 V   R   N   S   F   L   Q   E   S   W   G   E   E   E   R   N   I   T 819         828         837         846         855         864
TCT TTC CCA TTT AGT CCT GGG ATG TAC TTT GAG ATG ATA ATT TAC TGT GAT GTT
 S   F   P   F   S   P   G   M   Y   F   E   M   I   I   Y   C   D   V 873         882         891         900         909         918
AGA GAA TTC AAG GTT GCA GTA AAT GGC GTA CAC AGC CTG GAG TAC AAA CAC AGA
 R   E   F   K   V   A   V   N   G   V   H   S   L   E   Y   K   H   R 927         936         945         954         963         972
TTT AAA GAG CTC ARC AGT ATT TCA GCT GNA AAT TAA TGN GNC CAN CCN ATT NCT
 F   K   E   L   X   S   I   S   A   X   N   *

981         990         999        1008        1017        1026
GAG AAT ANA GAC NTT NGA CCT NCN TCA CAG AAG TTN TCA NAA AAC CNA AAA ATG 1035        1044        1053        1062        1071        1080
GAA GGT CTT TGT GNT AAN AGT TCC GTT GNT TAN AAN CTC TCA TCT TAN TTT ATT 3'
```

| Library | Lib Description | Abun | Pct Abun |
|---|---|---|---|
| HEARNOT01 | heart, 56 M | 3 | 0.2121 |
| PITUNOT02 | pituitary, 7-65 M/F | 1 | 0.0452 |
| MMLR1DT01 | macrophages (adher PBMNC), M/F, 24-hr MLR | 1 | 0.0235 |
| TMLR3DT01 | lymphocytes (non-adher PBMNC), M, 96-hr MLR | 1 | 0.0228 |
| LUNGFET03 | lung, fetal F | 1 | 0.0137 |

FIGURE 3

HUMAN GALECTIN HOMOLOG

FIELD OF THE INVENTION

The present invention relates to nucleic acid and amino acid sequences of a novel human galectin homolog and to the use of these sequences in the diagnosis, prevention and treatment of disease.

BACKGROUND OF THE INVENTION

Lectins are proteins which are defined by their ability to bind carbohydrates specifically and to agglutinate cells. Lectins have been shown to be involved in a wide variety of cellular functions including cell-cell and cell-matrix interactions. Lectins are widespread among plants, invertebrates and mammals.

Animal lectins have been grouped into four distinct families: 1) C-type lectins, which include selecting; 2) P-type lectins; 3) galectins (formerly termed S-type lectins or S-Lac lectins); and 4) pentraxins [Barondes S. H. et al. (1994) J. Biol. Chem. 269:20807–10]. The C-type lectins bind carbohydrate ligands in a $Ca^{2+}$-dependent manner and are structurally related to the asialoglycoprotein receptor. Selectins, a subcategory of the C-type lectins, are composite transmembrane molecules which are involved in cell-cell interactions. The selectins include lymphocyte homing receptors and platelet/endothelial cell surface receptors [Stoolman (1989) Cell 56:907–10].

Galectins bind specifically to β-galactoside residues in a thiol-dependent manner. To date eight galectin types have been identified (galectin-1 through galectin-8). In addition to their affinity for β-galactoside sugars, members of the galectin family share significant sequence similarity in the carbohydrate recognition domain (CRD; also referred to as the carbohydrate-binding domain). In most mammalian galectins, the CRD is encoded by 3 exons aid the majority of the residues conserved between galectins are encoded by the middle one of these three exons. Typically this region contains four β-strands and intervening loops (these β-strands are termed S3, S4, S5, and S6a/S6b according to Barondes S. H. et al., supra). Conserved residues or motifs located within the CRDs of mammalian galectins include $H_{45}$, $N_{47}$, $P_{48}$, $R_{49}$, $V_{56}$, $N_{58}$, $W_{65}$, $E_{68}$, $F_{76}$ and $G_{79}$ (numbering according to amino acid sequence of galectin-2 as shown in Barondes S. H. et al., supra). The importance of some of these conserved residues for binding carbohydrates has been confirmed by site-directed mutagenesis [Abbott and Feizi (1991) J. Biol. Chem. 266:5552–57 and Hirabayashi and Kasai (1991) J. Biol. Chem. 266:23648–53]. All mammalian galectins which have been analyzed in detail recognize the same structural determinant on lactose (primarily the galactose residue with significant interaction with the glucose residue) and related β-galactosides. In addition to binding β-galactoside sugars, galectins possess hemagglutination activity.

Despite the fact that the cellular milieu contains a large number of β-galactoside-containing glycoconjugates, few naturally occurring glycoconjugates have been shown to bind to specific galectins in vitro, suggesting that interactions between galectins and glycoconjugates are physiologically significant (i.e., galectins do not bind promiscuously to all naturally-occurring glycoconjugates). Laminin, a naturally occurring glycoprotein containing numerous polylactosamine chains, has been shown to be a natural ligand for galectin-1; galectin-3 has also been shown to bind laminin. Laminin is a component of the basal laminae, the extracellular matrix which underlies all epithelia and surrounds individual muscle, fat and Schwann cells. Interaction between cells and the basal laminae is known to influence the migration and/or differentiation of various cell types during mammalian development. Galectin-1 (also known as galaptin, L-14,L-14-I and BHL) is also known to bind to the polylactosamine-rich lysosome-associated membrane proteins (LAMPs) which can be found on the cell surface [Do K. Y. et al. (1991) Biochem. Biophys. Res. Commun. 173:1123–28 and Skrincosky D. M. et al. (1993 Cancer Res. 53:2667–75; Erratum (1993) Cancer Res. 53:3652], integrin $\alpha_7\beta_1$ present on skeletal muscle [Gu M. J. et al. (1994) J. Cell. Sci 107:175–81] and a lactosamine-containing glycolipid present on olfactory neurons [Mahanthappa N. K. et al. (1994) Development (Camb.) 120:1373–84]. Galectin-3 (also known as Mac-2, EPB, CBP-35, CBP-30 and L-29) has been shown to interact with immunoglobulin E (IgE) and the IgE receptor [Liu F. T. (1993) Immunol. Today 14:486–90 and Frigeri L. G. et al. (1993) Biochem. 32:7644–49, respectively].

Structure of Galectins

Galectin-1 and -2 exist as homodimers composed of subunits of approximately 130 amino acids (~14 kDa); each subunit forms one compact globular domain which possesses carbohydrate binding activity (i.e., the CRD) [Barondes S. H. et al. (1994), supra]. Galectin-3 has one CRD, a short N-terminal domain and an intervening proline, glycine and tyrosine-rich domain which consists of repeats of 7–10 conserved amino acids. These tandem repeats are characteristic of the collagen gene superfamily. The number of repeats varies between mammalian galectin-3 molecules and accounts for the differences in size between galectin-3 from different species of mammals. The N-terminal half of galectin-3 permits the molecule to undergo multimerization upon binding to surfaces containing glycoconjugate ligands. Galectin-4 exists as a monomer of about 36 kDa and has two CRDs connected by a link region that is homologous to the repeating domain of galectin-3 [Oda Y. et al. (1993) J. Biol. Chem. 268:5929–39. Human galectin-7 exists as a monomer of approximately 14 kDa [Magnaldo T. et al. (1995) Develop. Biol. 168:259–71 and Madsen P. et al. (1995) J. Biol. Chem. 270:5823–29]. Rat galectin-8 is a monomer of approximately 35 kDa and like galectin-4, has two CRDs in the same polypeptide chain joined by a short (~30 amino acids) link region [Hadari Y. R. et al. (1995) J. Biol. Chem. 270:3447–53]. The link region of rat galectin-8 is not similar to either the link region of galectin-4 or to the proline, glycine and tyrosine-rich repeat domain of galectin-3.

Nomenclature For Galectins

Galectins have been discovered in a variety of mammalian species and in a variety of contexts; this led to the use of multiple names for the same galectin. Recently a consensus on nomenclature for galectins was reached [Barondes S. H. et al. (1994), supra]. Individual mammalian galectins are now named by consecutive numbering (e.g., galectin-1). The genes encoding mammalian galectins are given the designation LGALS (lectin, galactoside-binding, soluble) followed by the number used to identify the protein (e.g., LGALS1).

Expression Of Mammalian Galectins

Galectins are expressed in a wide variety of tissues in mammals. The distribution of the different galectins is distinct but overlapping. Galectin-1 is expressed abundantly in muscle (skeletal, smooth and cardiac), neurons (both motor and sensory), thymus, kidney and placenta. Galectin-2 is expressed in hepatomas. Galectin-3 is expressed most highly in activated macrophages, basophils and mast cells; galectin-3 is also expressed in intestinal and kidney epithelial cells, vascular smooth muscle cells and in some sensory neurons. The expression of galectin-3 has been shown to be elevated in tumors [Raz A. and Lotan R. (1987) Cancer Metastasis Rev. 6:433]. Rat galectin-4 is expressed in intestinal epithelium and the stomach (a galectin-4 homolog has been isolated from nematodes). Human galectin-7 is expressed in keratinocytes and its expression is markedly downregulated in SV40 transformed keratinocytes and in malignant keratinocyte cell lines [Madsen P. et al. (1995), supra and Magnaldo T. et al. (1995), supra]. Rat galectin-8 is most highly expressed in lung with significant expression in liver, muscle (cardiac and skeletal) and spleen; low levels of galectin-8 are found in rat brain; expression of rat galectin-8 appears to be developmentally regulated as rat galectin-8 mRNA is expressed at very low levels in whole embryos while high levels of expression are found in adult rat tissues [Hadari Y. R. et al. (1995), supra].

Some galectins have been shown to be secreted (e.g., galectin-1, galectin-3 and galectin-7); however, all galectins characterized to date lack typical secretion signal peptides. There is direct evidence that some galectins are externalized by an atypical secretory mechanism. Galectins are not unique in being secreted by atypical secretory mechanisms; other secreted proteins such as interleukin-1, thymosin and fibroblast growth factor lack signal sequences.

Biological Activities Of Galectins

Galectins have been implicated in a wide variety of biological functions including cell adhesion, growth regulation, cell migration, neoplastic transformation and immune responses. Galectin-1 and -3 are the best characterized of the mammalian galectins. Galectin-1 is known to both promote and inhibit cell adhesion. In skeletal muscle, galectin-1 inhibits cell-matrix interaction and is thought to play a role in muscle development while in other cell types galectin-1 promotes cell-matrix adhesion. Galectin-1 has also been implicated in the regulation of cell proliferation and in some immune functions. Expression of galectin-1 has been shown to correlate with tumor metastasis potential [Raz A. et al. (1986) Cancer Res. 46:3667–72].

Like galectin-1, galectin-3 inhibits cell adhesion by binding to laminin. Galectin-3 plays a role in inflammation by binding to both IgE and the IgE receptor thereby causing activation of mast cells and basophils. Galectin-3 has been shown to concentrate in the nucleus of certain cell types during proliferation. Expression of galectin-3 is elevated in certain tumors, suggesting galectin-3 plays a role in metastasis. Indeed, overexpression of galectin-3 in a weakly metastatic cell line caused a significant increase in metastatic potential [Raz A. et al. (1990) Int. J. Cancer 46:871–77].

The expression of human galectin-7 appears to be limited to keratinocytes (Magnaldo T. et al., supra). Galectin-7 is thought to play a role in cell-matrix and cell-cell interactions as galectin-7 is found in areas of cell-cell contact (e.g., in the upper layers of human epidermis) and its expression is sharply downregulated in anchorage independent keratinocytes and is absent in a malignant keratinocyte cell line. Galectin-7 may be required for the maintenance of normal keratinocytes [Madsen P. et al., supra].

The expression of galectin-8 is developmentally regulated in the rat suggesting that galectin-8 regulates cell growth and embryogenesis. Rat galectin-8 is expressed in a wide variety of tissues in the adult including lung, liver, kidney, spleen and muscle (cardiac and skeletal) (Hadari Y. R. et al., supra).

Galectins represent an important family of proteins which are involved in regulating cell growth and development. Discovery of new molecules related to or in the mammalian galectin gene family is useful for the development of new diagnostic or therapeutic compositions.

SUMMARY

The present invention discloses a novel human galectin, hereinafter referred to as human galectin-8, which shares features with rat galectin-8 as well as other mammalian galectins which are involved in the regulation of cell growth and development, including metastatic potential. Accordingly, the invention provides a substantially purified polypeptide comprising at least a portion of the amino acid sequence of SEQ ID NO:1. In an alternative embodiment, the present invention provides fragments of isolated (i.e., substantially purified) human galectin-8 of at least 86 amino acid residues in length. The invention further contemplates fragments of isolated human galectin-8 of at least 100 amino acids, at least 150 amino acids, and at least 200 amino acids in length.

The present invention further provides an isolated polynucleotide sequence encoding a polypeptide comprising at least a portion of the amino acid sequence of SEQ ID NO:1. In a preferred embodiment, the isolated polynucleotide comprises at least a portion of the nucleic acid sequence of SEQ ID NO:2 or variants thereof. In another preferred embodiment, the present invention provides polynucleotides comprising fragments of SEQ ID NO:2 having a length greater than 259 nucleotides. The invention further contemplates fragments of this polynucleotide sequence (i.e., SEQ ID NO:2) that are at least 350 nucleotides, at least 500 nucleotides, and at least 1000 nucleotides in length.

In yet another embodiment, the present invention provides polynucleotide sequences comprising the complement of the nucleic acid sequence of SEQ ID NO:2 or variants thereof; these complementary nucleic acid sequences may comprise the complement of the entire nucleic acid sequence of SEQ ID NO:2 or fragments thereof.

In another embodiment, the present invention provides a polynucleotide sequence that hybridizes under stringent conditions to the nucleic acid sequence of SEQ ID NO:2.

The invention further contemplates the nucleic acid sequences encoding human galectin-8, oligonucleotides, peptide nucleic acids (PNA), fragments, portions or antisense molecules thereof.

The present invention also provides a method for detecting the presence of polynucleotide sequences encoding at least a portion of human galectin in a biological sample, comprising the steps of: a) providing: i) a biological sample suspected of containing nucleic acid corresponding to the polynucleotide sequence of SEQ ID NO:2; ii) the polynucleotide of SEQ ID NO:2, or a fragment thereof; b) combining the biological sample with the polynucleotide under conditions such that a hybridization complex is formed between the nucleic acid and the polynucleotide; and c) detecting the hybridization complex. The method of the present invention is not limited by the nature of the nucleic acid corresponding to the polynucleotide sequence of SEQ ID NO:2. In a preferred embodiment, the nucleic acid is ribonucleic acid (RNA) and the detection of a hybridization complex between SEQ ID NO:2 and the RNA correlates with expression of the polynucleotide of SEQ ID NO:2 in the biological sample. In another preferred embodiment, the nucleic acid corresponding to the polynucleotide sequence of SEQ ID NO:2 is deoxyribonucleic acid (DNA) and the detection of a hybridization complex between the DNA in a sample and SEQ ID NO:2 is performed under conditions that permit the detection of alterations (e.g., deletions, translocations, insertions, point mutations, etc.) in the polynucleotide of SEQ ID NO:2 in the biological sample.

The present invention further provides an antisense molecule comprising the nucleic acid sequence complementary to at least a portion of the polynucleotide of SEQ ID NO:2. In another embodiment, the present invention provides a pharmaceutical composition comprising an antisense molecule comprising the nucleic acid sequence complementary to at least a portion of the polynucleotide of SEQ ID NO:2 and a pharmaceutically acceptable excipient.

In another embodiment, the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an E. coli cell, a yeast cell, an insect cell, a mammalian cell, etc.

The present invention further provides a method for producing a polypeptide comprising the amino acid sequence of SEQ ID NO:1, the method comprising the steps of: a) culturing the host cell containing an expression vector containing an isolated polynucleotide comprising at least a portion of the nucleic acid sequence of SEQ ID NO:2 or variants thereof under conditions suitable for the expression of the polypeptide; and b) recovering the polypeptide from the host cell culture.

In another embodiment, the present invention provides a pharmaceutical composition comprising a substantially purified polypeptide comprising at least a portion of the amino acid sequence of SEQ ID NO:1 and a pharmaceutically acceptable excipient.

The present invention also provides a purified antibody which binds specifically to a polypeptide comprising at least a portion of the amino acid sequence of SEQ ID NO:1. The present invention further provides a pharmaceutical composition comprising a purified antibody which binds specifically to a polypeptide comprising at least a portion of the amino acid sequence of SEQ ID NO:1 and a pharmaceutically acceptable excipient.

The present invention also provides a method for detecting the expression of human galectin-8 in a biological sample comprising the steps of: a) providing: i) a biological sample suspected of expressing human galectin-8 protein; and ii) a purified antibody which binds specifically to a polypeptide comprising at least a portion of the amino acid sequence of SEQ ID NO:1; b) combining the biological sample and the antibody under conditions such that an antibody:protein complex is formed; and c) detecting the complex wherein the presence of the complex correlates with the expression of the protein in the biological sample.

BRIEF DESCRIPTION OF THE FIGURES

FIGS. 1A and 1B show the amino acid sequence (SEQ ID NO:1) and nucleic acid sequence (SEQ ID NO:2) of human galectin-8. The alignment was produced using MACDNA-SIS software (Hitachi Software Engineering Co Ltd, San Bruno, Calif.).

FIG. 2 shows the amino acid sequence alignment between human galectin-8 (SEQ ID NO:1) and rat galectin-8 [g717032 (SEQ ID NO:3); Hadari et al. (1995), supra]. These alignments were produced using the multisequence alignment program of DNASTAR software (DNAStar Inc, Madison Wis.).

FIG. 3 shows the northern analysis for Incyte Clone 305603 (SEQ ID NO:2). The northern analysis was produced electronically using the LIFESEQ database (Incyte Pharmaceuticals, Palo Alto, Calif.) and shows cDNA libraries in which sequences encoding human galectin-8 were expressed.

DESCRIPTION OF THE INVENTION

Definitions

To facilitate understanding of the invention, a number of terms are defined below.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence.

"Consensus" as used herein may refer to a nucleic acid sequence 1) which has been resequenced to resolve uncalled bases, 2) which has been extended using XL-PCR (Perkin Elmer, Norwalk Conn.) in the 5' or the 3' direction and resequenced, 3) which has been assembled from the overlapping sequences of more than one Incyte clone using the GCG fragment assembly system, (GCG, Madison Wis.), or 4) which has been both extended and assembled.

"Peptide nucleic acid" or "PNA" as used herein refers to a molecule which comprises an oligomer to which an amino acid residue, such as lysine, and an amino group have been added. These small molecules, also designated anti-gene agents, stop transcript elongation by binding to their complementary strand of nucleic acid [Nielsen P. E. et al. (1993) Anticancer Drug Des 8:53–63].

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring human galectin-8.

A "substitution" results from the replacement of one or more nucleotides or amino acids by different nucleotides or amino acids, respectively.

As used herein, "galectin-8" refers to the amino acid sequence of substantially purified galectin-8 obtained from any species, particularly mammalian, including bovine, ovine, porcine, murine, equine, and preferably human, from any source whether natural, synthetic, semi-synthetic or recombinant.

A "variant" of galectin-8 is defined as an amino acid sequence differs by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNASTAR software. Furthermore, as described herein, certain amino acid residues which are highly conserved among mammalian galectins are located within the CRDs and are implicated in binding β-galactoside sugars. It is preferred that these conserved residues not be substituted, inserted or deleted when producing variants of human galectin-8.

The term "biologically active" refers to a galectin-8 molecule having structural, regulatory or biochemical functions of a naturally occurring galectin-8 molecule. Likewise, "immunologically active" defines the capability of the natural, recombinant or synthetic galectin-8, or any oligopeptide thereof, to induce a specific immune response in appropriate animals or cells and to bind with specific antibodies.

The term "derivative" as used herein refers to the chemical modification of a nucleic acid encoding galectin-8 or the encoded galectin-8. Illustrative of such modifications would be replacement of hydrogen by an alkyl, acyl, or amino group. A nucleic acid derivative would encode a polypeptide which retains essential biological characteristics of natural human galectin-8.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

"Amplification" is defined as the production of additional copies of a nucleic acid sequence and is generally carried out using polymerase chain reaction technologies well known in the art [Dieffenbach C. W. and G. S. Dveksler (1995) *PCR Primer, a Laboratory Manual*, Cold Spring Harbor Press, Plainview N.Y.].

The term "hybridization" as used herein refers to any process by which a strand of nucleic acid joins with a complementary strand through base pairing.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5× SSPE, 0.1% SDS at 42° C. when a probe of about 500 nucleotides in length is employed.

High stringency conditions comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1× SSPE, 1.0% SDS at 42° C. when a probe of about 500 nucleotides in length is employed.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" [Coombs J. (1994) *Dictionary of Biotechnology*, Stockton Press, New York N.Y.].

"Stringency" typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human galectin-8 but not to sequences encoding the rat galectin-8 (i.e., SEQ ID NO:4 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NO:4) are preferentially employed.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) is sometimes used in reference to the antisense (i.e., "negative") strand, with the designation (+) sometimes used in reference to the sense (i.e., "positive") strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length human galectin-8 protein and fragments thereof.

The term "antigenic determinant" as used herein refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

The term "sample" as used herein is used in its broadest sense. A biological sample suspected of containing nucleic acid encoding human galectin-8 may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "correlates with expression of a polynucleotide" as used herein indicates that the detection of the presence of ribonucleic acid complementary to SEQ ID NO:2 by hybridization assays is indicative of the presence of mRNA encoding human galectin-8 in a sample and thereby correlates with expression of the galectin-8 mRNA from the gene encoding galectin-8.

"Alterations in the polynucleotide of SEQ ID NO:2" as used herein comprise any alteration in the sequence of polynucleotides encoding human galectin-8 including deletions, insertions, and point mutations that may be detected using hybridization assays. Included within this definition is the detection of alterations to the genomic DNA sequence which encodes human galectin-8 [e.g., by alterations in pattern of restriction enzyme fragments capable of hybridizing to SEQ ID NO:2 (RFLP analysis), the inability of a selected fragment of SEQ ID NO:2 to hybridize to a sample of genomic DNA (e.g., using allele-specific oligonucleotide probes), improper or unexpected hybridization, such as hybridization to a locus other than the normal chromosomal locus for the LGALS8 gene (e.g., using FISH to metaphase chromosomes spreads, etc.)].

Preferred Embodiments

Given the role galectins play in regulating cell growth and development, the discovery of new molecules related to or in the galectin gene family, and in the human galectin gene family in particular, is useful for developing diagnostic or therapeutic compositions directed at detecting or preventing neoplasia and/or metastasis. In addition, galectins are implicated in immune and inflammatory responses and thus novel human galectin genes are useful for developing diagnostic or therapeutic compositions directed at modulation of inflammation and immune responses.

The present invention relates to a novel human galectin-8 which was initially identified among the partial cDNAs from a heart library (HEARNOT01) and to the use of the disclosed nucleic acid and amino acid sequences in the study, diagnosis, prevention and treatment of disease.

The nucleic acid sequence encoding a portion of the novel human galectin-8 protein was identified in Incyte Clone 305603 through a computer-generated search for amino acid sequence alignments. The nucleic acid sequence, SEQ ID NO:2, disclosed herein, encodes the amino acid sequence, SEQ ID NO:1, human galectin-8 (FIG. 2). The full length cDNA was extended and assembled from Incyte Clones 305603 (HEARNOT01); 473598H1 (MMLR1DT01); and 533093H1 (BRAINOT03) from the LIFESEQ database (Incyte Pharmaceuticals, Palo Alto, Calif.).

The human galectin-8 of the present invention is here described as having 264 amino acid residues, a number of which are residues shown to be conserved among mammalian galectins in general (and among rat and human galectin-8, in particular) and which are implicated in the binding of β-galactoside sugars; these residues include $H_{65}$, $F_{66}$, $N_{67}$, $P_{68}$, $R_{69}$, $V_{77}$, $C_{78}$, $N_{79}$, $W_{86}$, $G_{87}$, $E_{90}$, $I_{91}$, $P_{96}$, $F_{97}$, $E_{104}$, $V_{106}$, $H_{189}$, $N_{191}$, $P_{192}$, $R_{193}$, $L_{194}$, $V_{200}$, $R_{201}$, $N_{202}$, $W_{209}$, $G_{210}$, $E_{212}$, $R_{214}$, $P_{220}$, and $F_{221}$.

The human galectin-8 of the present invention contains five cysteine residues ($C_{36}$, $C_{75}$, $C_{78}$, $C_{144}$ and $C_{233}$); three of these five cysteine residues (i.e., $C_{75}$, $C_{78}$, and $C_{233}$) are conserved between the human and rat galectin-8 proteins (see alignment shown in FIG. 2). While overall the primary structure of human and rat galectin-8 resembles that of galectin-4 most closely, the presence of cysteine residues is characteristic of mammalian galectin-1 and galectin-2 proteins; galectin-4 lacks cysteine. The human galectin-8 of the present invention has two potential N-linked glycosylation sites (i.e., Asn-X-Ser/Thr) (i.e., $N_{52}$ and $N_{215}$). The human galectin-8 protein appears to lack a transmembrane segment; a feature shared with other mammalian galectins.

Like rat galectin-8, human galectin-8 appears to comprise two CRDs within a single polypeptide chain wherein these two CRD domains are connected by a link region. The two CRDs of human galectin-8 are somewhat shorter that the corresponding rat galectin-8 CRDs (the human galectin-8 protein comprises 264 amino acids while the rat galectin-8 protein comprises 316 amino acids). Human galectin-8 is missing a region of 40 residues at the end of the N-terminal CRD and 13 residues at the end of the C-terminal CRD relative to the rat galectin-8 sequence (see FIG. 2). In all other regions, however, human galectin-8 shares a high degree of amino acid identity with the rat galectin-8 protein; 205 of the 264 amino acids (77.6%) in the human galectin-8 protein are identical to the rat galectin-8 protein. The human galectin-8 of the present invention, like the rat galectin-8, contains sequence motifs found within the CRDs derived from a variety of mammalian galectins (e.g., H-NPR). However, both the human galectin-8 of the present invention and the rat galectin-8 contain within their respective N-terminal CRDs the sequence WG-E-I in place of the consensus WG-E-R which is found in the CRDs of most mammalian galectins. The WG-E-R consensus sequence is found in the C-terminal CRD of both the human galectin-8 of the present invention and the rat galectin-8. The arginine residue (R) within the WG-E-R consensus sequence has been shown to play an important role in the interaction of galectins and the glucose residue of lactose [Lobsanov Y. D. et al (1993) J. Biol. Chem. 268:27034–38]. The substitution of isoleucine (I) for this arginine residue in the N-terminal CRD of the human and rat galectin-8 proteins may indicate that the N-terminal and C-terminal CRDs of mammalian galectin-8 have different sugar-binding specificities (Hadari Y. R. et al, supra). In this respect, galectin-8 is similar to galectin-4 as galectin-4 contains two CRDs having distinct structures and sugar-binding specificities [Hirabayashi J. et al. (1992) J. Biol. Chem. 267:15485–90].

The Human Galectin-8 Coding Sequences

The nucleic acid and deduced amino acid sequences of human galectin-8 are shown in FIGS. 1A and 1B. In accordance with the invention, any nucleic acid sequence which encodes human galectin-8 can be used to generate recombinant molecules which express human galectin-8. In a specific embodiment described herein, a partial sequence encoding human galectin-8 was first isolated as Incyte Clone 305603H1 from a heart cDNA library (HEARNOT01).

It will be appreciated by those skilled in the art that as a result of the degeneracy of the genetic code, a multitude of human galectin-8-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring human galectin-8, and all such variations are to be considered as being specifically disclosed.

Although nucleotide sequences which encode human galectin-8 and its variants are preferably capable of hybridizing to the nucleotide sequence of the naturally occurring sequence under appropriately selected conditions of stringency, it may be advantageous to produce nucleotide sequences encoding human galectin-8 or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding human galectin-8 and its derivatives without altering the encoded amino acid sequences include the production of RNA transcripts having more desirable properties, such as a greater or a shorter half-life, than transcripts produced from the naturally occurring sequence.

It is now possible to produce a DNA sequence, or portions thereof, encoding human galectin-8 and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding human galectin-8 or any portion thereof.

Also included within the scope of the present invention are polynucleotide sequences that are capable of hybridizing to the nucleotide sequence of FIGS. 1A and 1B under various conditions of stringency. Hybridization conditions are based on the melting temperature ($T_m$) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined "stringency".

Altered nucleic acid sequences encoding human galectin-8 which may be used in accordance with the invention include deletions, insertions or substitutions of different nucleotides resulting in a polynucleotide that encodes the same or a functionally equivalent human galectin-8. The protein may also show deletions, insertions or substitutions of amino acid residues which produce a silent change and result in a functionally equivalent human galectin-8. Deliberate amino acid substitutions may be made on the basis of similarity in polarity, charge, solubility, hydrophobicity, hydrophilicity, and/or the amphipathic nature of the residues as long as the biological activity of human galectin-8 is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding human galectin-8. As used herein, an "allele" or "allelic sequence" is an alternative form of the nucleic acid sequence encoding human galectin-8. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (U.S. Biochemical Corp, Cleveland Ohio), Taq DNA polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; M. J. Research, Watertown Mass.) and the ABI 377 DNA sequencers (Perkin Elmer).

Extending The Polynucleotide Sequence

The polynucleotide sequence encoding human galectin-8 may be extended utilizing partial nucleotide sequence and various methods known in the art to detect upstream sequences such as promoters and regulatory elements.

Gobinda et al. (1993; PCR Methods Applic 2:318–22) describe "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T. et al. (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M. et al. (1991) PCR Methods Applic 1:111–19), a method for PCR amplification of DNA fragments adjacent to a known sequence in human and yeast artificial chromosome DNA, may also be used. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J. D. et al. (1991) Nucleic Acids Res 19:3055–60), a method for targeted gene walking. Alternatively, PCR, nested primers, PROMOTERFINDER (Clontech, Palo Alto Calif.) and PROMOTERFINDER libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (e.g. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported [Ruiz-Martinez M. C. et al. (1993) Anal Chem 65:2851–8].

Expression Of The Nucleotide Sequence

In accordance with the present invention, polynucleotide sequences which encode human galectin-8, fragments of the polypeptide, fusion proteins or functional equivalents thereof may be used in recombinant DNA molecules that direct the expression of human galectin-8 in appropriate host cells. Due to the inherent degeneracy of the genetic code, other DNA sequences which encode substantially the same or a functionally equivalent amino acid sequence, may be used to clone and express human galectin-8. As will be understood by those of skill in the art, it may be advantageous to produce human galectin-8-encoding nucleotide sequences possessing non-naturally occurring codons. Codons preferred by a particular prokaryotic or eukaryotic host [Murray E. et al. (1989) Nuc Acids Res 17:477–508] can be selected, for example, to increase the rate of human galectin-8 expression or to produce recombinant RNA transcripts having desirable properties, such as a longer or a shorter half-life, than transcripts produced from naturally occurring sequence.

The nucleotide sequences of the present invention can be engineered in order to alter a human galectin-8-encoding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns, to change codon preference, to produce splice variants, etc.

In another embodiment of the invention, a natural, modified or recombinant human galectin-8-encoding sequence may be ligated to a heterologous sequence to encode a fusion protein. For example, for screening of peptide libraries for inhibitors of human galectin-8 activity, it may be useful to encode a chimeric human galectin-8 protein that is recognized by a commercially available antibody. A fusion protein may also be engineered to contain a cleavage site located between a human galectin-8 and the heterologous protein sequence, so that the human galectin-8 may be cleaved and substantially purified away from the heterologous moiety.

In an alternate embodiment of the invention, the sequence encoding human galectin-8 may be synthesized, whole or in part, using chemical methods well known in the art [see Caruthers M. H. et al. (1980) Nuc Acids Res Symp Ser 215–23, Horn T. et al. (1980) Nuc Acids Res Symp Ser 225–32, etc.]. Alternatively, the protein itself could be produced using chemical methods to synthesize a human galectin-8 amino acid sequence, whole or in part. For example, peptide synthesis can be performed using various solid-phase techniques [Roberge J. Y. et al. (1995) Science 269:202–204] and automated synthesis may be achieved, for example, using the ABI 431A peptide synthesizer (Perkin Elmer) in accordance with the instructions provided by the manufacturer.

The newly synthesized peptide can be substantially purified by reparative high performance liquid chromatography [e.g., Creighton (1983) *Proteins, Structures and Molecular Principles*, W. H. Freeman and Co, New York N.Y.]. The composition of the synthetic peptides may be confirmed by amino acid analysis or sequencing (e.g., the Edman degradation procedure; Creighton, supra). Additionally the amino acid sequence of human galectin-8, or any part thereof, may be altered during direct synthesis and/or combined using chemical methods with sequences from other proteins, or any part thereof, to produce a variant polypeptide.

Expression Systems

In order to express a biologically active human galectin-8, the nucleotide sequence encoding human galectin-8 or its functional equivalent, is inserted into an appropriate expression vector, i.e., a vector which contains the necessary elements for the transcription and translation of the inserted coding sequence.

Methods which are well known to those skilled in the art can be used to construct expression vectors containing a human galectin-8-encoding sequence and appropriate transcriptional or translational controls. These methods include in vitro recombinant DNA techniques, synthetic techniques and in vivo recombination or genetic recombination. Such techniques are described in Sambrook et al. (1989) *Molecular Cloning, A Laboratory Manual*, Cold Spring Harbor Press, Plainview N.Y. and Ausubel F. M. et al. (1989) *Current Protocols in Molecular Biology*, John Wiley & Sons, New York N.Y.

A variety of expression vector/host systems may be utilized to contain and express a human galectin-8-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificities and are those nontranslated regions of the vector, enhancers, promoters, and 3' and 5' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla Calif.) or PSPORT1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of the sequence encoding human galectin-8, vectors based on SV40 or EBV may be used with an appropriate selectable marker.

In bacterial systems, a number of expression vectors may be selected depending upon the use intended for human galectin-8. For example, when large quantities of human galectin-8 are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the sequence encoding human galectin-8 may be ligated into the vector in frame with sequences for the amino-terminal Met and the subsequent 7 residues of β-galactosidase so that a hybrid protein is produced; pIN vectors [Van Heeke & Schuster (1989) J. Biol Chem 264:5503–5509]; and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al. (supra) and Grant et al. (1987) Methods in Enzymology 153:516–544.

In cases where plant expression vectors are used, the expression of a sequence encoding human galectin-8 may be driven by any of a number of promoters. For example, viral promoters such as the 35S and 19S promoters of CaMV [Brisson et al. (1984) Nature 310:511–514] may be used alone or in combination with the omega leader sequence from TMV [Takamatsu et al. (1987) EMBO J. 6:307–311]. Alternatively, plant promoters such as the small subunit of RUBISCO [Coruzzi et al. (1984) EMBO J. 3:1671–1680; Broglie et al. (1984) Science 224:838–843]; or heat shock promoters [Winter J. and Sinibaldi R. M. (1991) Results Probl Cell Differ 17:85–105] may be used. These constructs can be introduced into plant cells by direct DNA transformation or pathogen-mediated transfection. For reviews of such techniques, see Hobbs S. or Murry L. E. in *McGraw Hill Yearbook of Science and Technology* (1992) McGraw Hill New York N.Y., pp 191–196, or Weissbach and Weissbach (1988) *Methods for Plant Molecular Biology*, Academic Press, New York N.Y., pp 421–463.

An alternative expression system which could be used to express human galectin-8 is an insect system. In one such system, *Autographa californica* nuclear polyhedrosis virus (AcNPV) is used as a vector to express foreign genes in *Spodoptera frugiperda* cells or in *Trichoplusia larvae*. The sequence encoding human galectin-8 may be cloned into a nonessential region of the virus, such as the polyhedrin gene, and placed under control of the polyhedrin promoter. Successful insertion of the sequence encoding human galectin-8 will render the polyhedrin gene inactive and produce recombinant virus lacking coat protein. The recombinant viruses are then used to infect *S. frugiperda* cells or *Trichoplusia larvae* in which human galectin-8 is expressed [Smith et al. (1983) J. Virol 46:584; Engelhard E. K. et al. (1994) Proc Nat Acad Sci 91:3224–7].

In mammalian host cells, a number of viral-based expression systems may be utilized. In cases where an adenovirus is used as an expression vector, a sequence encoding human galectin-8 may be ligated into an adenovirus transcription/translation complex consisting of the late promoter and tripartite leader sequence. Insertion in a nonessential E1 or E3 region of the viral genome will result in a viable virus capable of expressing in infected host cells [Logan and Shenk (1984) Proc Natl Acad Sci 81:3655–59]. In addition, transcription enhancers, such as the rous sarcoma virus (RSV) enhancer, may be used to increase expression in mammalian host cells.

Specific initiation signals may also be required for efficient translation of a sequence encoding human galectin-8. These signals include the ATG initiation codon and adjacent sequences. In cases where the sequence encoding human galectin-8, its initiation codon and upstream sequences are inserted into the most appropriate expression vector, no additional translational control signals may be needed. However, in cases where only coding sequence, or a portion thereof, is inserted, exogenous translational control signals including the ATG initiation codon, and termination codons must be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use [Scharf D. et al. (1994) Results Probl Cell Differ 20:125–62; Bittner et al. (1987) Methods in Enzymol 153:516–544].

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express human galectin-8 may be transformed using expression vectors which contain endogenous expression elements, and may also contain viral origins of replication and a selectable marker gene; the selectable marker gene may be located on the same vector as the galectin-8-encoding sequences or may be located on a separate vector which contains sequences which permit expression of the selectable marker gene. Following the introduction of the vector(s), cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transfected cells can be proliferated using tissue culture techniques appropriate to the cell type.

Any number of selection systems may be used to recover transfected cell lines. These include, but are not limited to, the herpes simplex virus thymidine kinase (Wigler M. et al. (1977) Cell 11:223–32) and adenine phosphoribosyltransferase (Lowy I. et al. (1980) Cell 22:817–23) genes which can be employed in tk- or aprt- cells, respectively. Also, antimetabolite, antibiotic or herbicide resistance can be used as the basis for selection; for example, dhfr, which confers resistance to methotrexate [Wigler M. et al. (1980) Proc Natl Acad Sci 77:3567–70]; npt, which confers resistance to the aminoglycosides neomycin and G-418 [Colbere-Garapin F. et al. (1981) J Mol Biol 150:1–14]; and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine [Hartman S. C. and R. C. Mulligan (1988) Proc Natl Acad Sci 85:8047–51]. Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system [Rhodes C. A. et al. (1995) Methods Mol Biol 55:121–131].

Identification Of Transfectants Containing The Polynucleotide Sequence

Although the presence/absence of marker gene expression suggests that the gene of interest is also present, its presence and expression should be confirmed. For example, if the sequence encoding human galectin-8 is inserted within a marker gene sequence, recombinant cells containing the sequence encoding human galectin-8 can be identified by the absence of marker gene function. Alternatively, a marker gene can be placed in tandem with the sequence encoding human galectin-8 under the control of a single promoter. Expression of the marker gene in response to induction or selection usually indicates expression of the tandem sequence as well.

Alternatively, host cells which contain the coding sequence for human galectin-8 and express human galectin-8 may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding human galectin-8 can be detected by DNA-DNA or DNA-RNA hybridization or amplification using probes, portions or fragments of the sequence encoding human galectin-8. Nucleic acid amplification based assays involve the use of oligonucleotides or oligomers based on the nucleic acid sequence to detect transformants containing DNA or RNA encoding human galectin-8. As used herein "oligonucleotides" or "oligomers" refer to a nucleic acid sequence of at least about 10 nucleotides and as many as about 60 nucleotides, preferably about 15 to 30 nucleotides, and more preferably about 20 to 25 nucleotides which can be used as a probe or amplimer.

A variety of protocols for detecting and measuring the expression of human galectin-8, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on human galectin-8 is preferred, but a competitive binding assay may be employed. These and other assays are described, among other places, in Hampton R. et al. (1990, *Serological Methods a Laboratory Manual*, APS Press, St Paul Minn.) and Maddox D. E. et al. (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the human galectin-8-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

Purification Of Human Galectin-8

Host cells transformed with a nucleotide sequence encoding human galectin-8 may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing human galectin-8-encoding sequence can be designed with signal sequences which direct secretion of human galectin-8 through a prokaryotic or eukaryotic cell membrane.

Human galectin-8 may also be expressed as a recombinant protein with one or more additional polypeptide domains added to facilitate purification of soluble proteins. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and human galectin-8 is useful to facilitate purification. One such expression vector provides for expression of a fusion protein comprising the sequence encoding human galectin-8 and nucleic acid sequence encoding 6 histidine residues followed by thioredoxin and an enterokinase cleavage site. The histidine residues facilitate purification while the enterokinase cleavage site provides a means for purifying human galectin-8 from the fusion protein. Literature pertaining to vectors containing fusion proteins is available in the art [see, for example, Kroll D. J. et al. (1993) DNA Cel Biol 12:441–53].

In addition to recombinant production, fragments of human galectin-8 may be produced by direct peptide synthesis using solid-phase techniques [cf Stewart et al. (1969) *Solid-Phase Peptide Synthesis*, W. H. Freeman Co, San Francisco; Merrifield J. (1963) J Am Chem Soc 85:2149–2154]. In vitro protein synthesis may be performed using manual techniques or by automation. Automated synthesis may be achieved, for example, using Applied Biosystems 431A peptide synthesizer (Perkin Elmer, Foster City Calif.) in accordance with the instructions provided by the manufacturer. Various fragments of human galectin-8 may be chemically synthesized separately and combined using chemical methods to produce the full length molecule.

Uses Of Human Galectin-8

The rationale for use of the nucleotide and peptide sequences disclosed herein is based in part on the chemical and structural homology among the novel human galectin-8 protein and rat galectin-8 [g717032; Hadari Y. R. et al. (1995), supra]. In addition the novel human galectin-8 protein shares structural features with other mammalian galectins, including galectin-1, whose overexpression has been shown to correlate with metastatic potential [Raz A. et al. (1986), supra]. In addition, as shown herein, human galectin-8 is expressed in human monocytic THP-1 cells treated with the phorbol ester phorbol 12-myistate 13-acetate (PMA). Phorbol esters act as tumor promoters by persistently activating signalling pathways involved in cell proliferation (e.g., activation of protein kinase C). The THP-1 cell line (ATCC TIB 202) was derived from a patient with acute monocytic leukemia. The presence of mRNA transcripts encoding human galectin-8 in the THP-1 cell line suggests that human galectin-8, like other mammalian galectins, plays a role in neoplastic transformation.

In addition, human galectin-8 was found to expressed in both macrophages and lymphocytes isolated from mixed lymphocyte reactions (MLRs) indicating that human galectin-8 plays a role in immune responses [the MLR is considered to be the in vitro correlate of graft rejection [Basic & Clinical Immunology, Stites D. P. et al., Eds (1984) Lange Medical Publications, Los Atos, Calif., p. 100]. Lymphocytes and macrophages isolated from positive MLRs are said to be "activated" and the activation is presumably HLA-mediated. Transcripts which are abundant in positive MLRs are indicative of gene expression induced by antigen-activated cells. Activated lymphocytes and macrophages are seen in a variety of inflammatory responses including graft-vs-host (GVH) rejection, infection and nonspecific inflammation such as that caused by drug reactions.

The expression of human galectin-8 in monocytic leukemia cell lines and in activated lymphocytes makes the nucleic and amino acid sequences useful in the development of diagnostics for tumors and immune/inflammatory responses (including GVH). The nucleotide sequence may be used in hybridization or PCR technologies to diagnose the induced expression of protective native sequences early in the disease process. Likewise the protein can be used to produce antibodies useful in ELISA assays or a derivative diagnostic format.

The nucleotide sequence encoding human galectin-8 is useful when placed in an expression vector for making quantities of protein for therapeutic use. The antisense nucleotide sequence of the human LGALS8 gene is potentially useful in vectors designed for gene therapy directed at neoplasia including metastases. Additionally, the inhibition of human galectin-8 expression may be useful in alleviating GVH disease or reducing other immune or inflammatory responses. Alternatively, the human galectin-8-encoding nucleotide sequence may used to direct the expression of human galectin-8 in situations where it is desirable to increase the immune response (e.g., administration of vaccines, treatment of immunocompromised patients, etc.). Even the transient expression or delivery of human galectin-8 to cells and tissues may be therapeutic.

Human Galectin-8 Antibodies

Human galectin-8-specific antibodies are useful for the diagnosis and treatment of conditions and diseases associated with expression of human galectin-8 (including the overexpression and the absence of expression). Such antibodies include, but are not limited to, polyclonal, monoclonal, chimeric, single chain, Fab fragments and fragments produced by a Fab expression library. Neutralizing antibodies, i.e., those which inhibit dimer formation, are especially preferred for diagnostics and therapeutics.

Human galectin-8 protein to be used for antibody induction need not retain biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of human galectin-8 amino acids may be fused with those of another protein such as keyhole limpet hemocyanin and antibody produced against the chimeric molecule.

For the production of antibodies, various hosts including goats, rabbits, rats, mice, etc may be immunized by injection with human galectin-8 or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Monoclonal antibodies to human galectin-8 may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al. (1983) Immunol Today 4:72; Cote et al (1983) Proc Natl Acad Sci 80:2026–2030) and the EBV-hybridoma technique [Cole et al. (1985) *Monoclonal Antibodies and Cancer Therapy*, Alan R. Liss Inc, New York N.Y., pp 77–96].

In addition, techniques developed for the production of "chimeric antibodies", the splicing of mouse antibody genes to human antibody genes to obtain a molecule with appropriate antigen specificity and biological activity can be used [Morrison et al. (1984) Proc Natl Acad Sci 81:6851–6855; Neuberger et al. (1984) Nature 312:604–608; Takeda et al. (1985) Nature 314:452–454]. Alternatively, techniques described for the production of single chain antibodies (U.S. Pat. No. 4,946,778) can be adapted to produce human galectin-8-specific single chain antibodies.

Antibodies may also be produced by inducing in vivo production in the lymphocyte population or by screening recombinant immunoglobulin libraries or panels of highly specific binding reagents as disclosed in Orlandi et al. (1989, Proc Natl Acad Sci 86: 3833–3837), and Winter G. and Milstein C. (1991; Nature 349:293–299).

Antibody fragments which contain specific binding sites for human galectin-8 may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity [Huse W. D. et al. (1989) Science 256:1275–1281].

A variety of protocols for competitive binding or immunoradiometric assays using either polyclonal or monoclonal antibodies with established specificities are well known in the art. Such immunoassays typically involve the formation of complexes between human galectin-8 and its specific antibody and the measurement of complex formation. A two-site, monoclonal-based immunoassay utilizing monoclonal antibodies reactive to two noninterfering epitopes on a specific human galectin-8 protein is preferred, but a competitive binding assay may also be employed. These assays are described in Maddox D. E. et al. (1983, J Exp Med 158:1211).

Diagnostic Assays Using Human Galectin-8 Specific Antibodies

Particular human galectin-8 antibodies are useful for the diagnosis of conditions or diseases characterized by expression of human galectin-8 or in assays to monitor patients being treated with human galectin-8, its fragments, agonists or inhibitors (including antisense transcripts capable of reducing expression of human galectin-8). Diagnostic assays for human galectin-8 include methods utilizing the antibody and a label to detect human galectin-8 in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring human galectin-8, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two noninterfering epitopes on human galectin-8 is preferred, but a competitive binding assay may be employed. These assays are described, among other places, in Maddox, D. E. et al. (1983, J Exp Med 158:1211).

In order to provide a basis for diagnosis, normal or standard values for human galectin-8 expression must be established. This is accomplished by combining body fluids or cell extracts taken from normal subjects, either animal or human, with antibody to human galectin-8 under conditions suitable for complex formation which are well known in the art. The amount of standard complex formation may be quantified by comparing various artificial membranes containing known quantities of human galectin-8 with both control and disease samples from biopsied tissues. Then, standard values obtained from normal samples may be compared with values obtained from samples from subjects potentially affected by disease (e.g., metastases or GVH or other inflammatory conditions). Deviation between standard and subject values establishes the presence of disease state.

Drug Screening

Human galectin-8, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between human galectin-8 and the agent being tested, may be measured.

Another technique for drug screening which may be used for high throughput screening of compounds having suitable binding affinity to the human galectin-8 is described in detail in "Determination of Amino Acid Sequence Antigenicity" by Geysen H. N., WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of human galectin-8 and washed. Bound human galectin-8 is then detected by methods well known in the art. Substantially purified human galectin-8 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding human galectin-8 specifically compete with a test compound for binding human galectin-8. In this manner, the antibodies can be used to detect the presence of any peptide which shares one or more antigenic determinants with human galectin-8.

Diagnostic and Therapeutic Uses Of The Polynucleotide Encoding Human Galectin-8

A polynucleotide sequence encoding human galectin-8 or any part thereof may be used for diagnostic and/or therapeutic purposes. For diagnostic purposes, the sequence encoding human galectin-8 of this invention may be used to detect and quantitate gene expression in biopsied tissues in which human galectin-8 may be expressed. The diagnostic assay is useful to distinguish between absence, presence, and excess expression of human galectin-8 and to monitor regulation of human galectin-8 levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding human galectin-8 or closely related molecules. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate or low) will determine whether the probe identifies only naturally occurring human galectin-8, alleles or related sequences.

Probes may also be used for the detection of related sequences and should preferably contain at least 50% of the nucleotides from any of these human galectin-8-encoding sequences. The hybridization probes of the subject invention may be derived from the nucleotide sequence of SEQ ID NO:2 or from genomic sequence including promoter, enhancer elements and introns of the naturally occurring sequence encoding human galectin-8. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

Other means for producing specific hybridization probes for DNAs include the cloning of nucleic acid sequences encoding human galectin-8 or human galectin-8 derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding human galectin-8 may be used for the diagnosis of conditions or diseases with which the expression of human galectin-8 is associated. For example, polynucleotide sequences encoding human galectin-8 may be used in hybridization or PCR assays of fluids or tissues from biopsies to detect human galectin-8 expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The human galectin-8-encoding nucleotide sequences disclosed herein provide the basis for assays that detect activation or induction associated with inflammation or disease (including metastasis). The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding human galectin-8 in the sample indicates the presence of the associated inflammation and/or disease. Alternatively, the loss of expression of human galectin-8 sequences in a tissue which normally expresses human galectin-8 sequences indicates the presence of an abnormal or disease state.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for human galectin-8 expression must be established. This is accomplished by combining body fluids or cell extracts taken from normal subjects, either animal or human, with human galectin-8, or a portion thereof, under conditions suitable for hybridization or amplification. Standard hybridization may be quantified by comparing the values obtained for normal subjects with a dilution series of human galectin-8 run in the same experiment where a known amount of substantially purified human galectin-8 is used. Standard values obtained from normal samples may be compared with values obtained from samples from patients affected by human galectin-8-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used and provides additional uses for oligonucleotides based upon the sequence encoding human galectin-8. Such oligomers are generally chemically synthesized, but they may be generated enzymatically or produced from a recombinant source. Oligomers generally comprise two nucleotide sequences, one with sense orientation (5'→3') and one with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling [Melby P. C. et al. (1993) J Immunol Methods 159:235–44] or biotinylating [Duplaa C. et al. (1993) Anal Biochem 212:229–236] nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Based upon its homology to mammalian galectins and its expression profile (e.g., expression in lymphocytes and macrophages in MLRs), the polynucleotide encoding human galectin-8 disclosed herein may be useful for increasing the immune response. Stimulation of immune responses is desirable in the context of administration of vaccines (for example, current vaccine protocols involve the addition of various cytokines for the purpose of increasing the response to a particular antigen by stimulation of the immune response) or the treatment of immunocompromised patients (e.g., patients having AIDS, undergoing chemotherapy, malnourished, etc.). In addition, as human galectin-8 appears to be expressed in certain human tumor cell lines (e.g., HepG2 and THP-1) and overexpression of other galectins have been shown to correlate with metastatic potential, inhibition of human galectin-8 expression may be therapeutic.

Expression vectors derived from retroviruses, adenovirus, herpes or vaccinia viruses, or from various bacterial plasmids, may be used for delivery of nucleotide sequences (sense or antisense) to the targeted organ, tissue or cell population. Methods which are well known to those skilled in the art can be used to construct recombinant vectors which will express antisense of the sequence encoding human galectin-8. See, for example, the techniques described in Sambrook et al. (supra) and Ausubel et al. (supra).

The polynucleotides comprising full length cDNA sequence and/or its regulatory elements enable researchers to use the sequence encoding human galectin-8 as an investigative tool in sense [Youssoufian H. and H. F. Lodish 1993 Mol Cell Biol 13:98–104] or antisense [Eguchi et al. (1991) Annu Rev Biochem 60:631–652] regulation of gene function. Such technology is now well known in the art, and sense or antisense oligomers, or larger fragments, can be designed from various locations along the coding or control regions.

Genes encoding human galectin-8 can be turned off by transfecting a cell or tissue with expression vectors which express high levels of a desired human galectin-8 fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the sequence encoding human galectin-8, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al. (In: Huber B. E. and B. I. Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding human galectin-8.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding human galectin-8. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding human galectin-8 disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding human galectin-8 can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization (FISH) of chromosome spreads has been described, among other places, in Verma et al. (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding human galectin-8 on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research [Hudson T. J. et al. (1995) Science 270:1945–1954]. Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxiate-langiectasia (AT), has been crudely localized by genetic linkage to a particular genomic region, for example, AT to 11q22–23 [Gatti et al. (1988) Nature 336:577–580], any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, e.g., by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, and succinic acids, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of human galectin-8, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, e.g., tumor size and location; age, weight and gender of the patient; diet, time and frequency of administration, drug combination(s), reaction sensitivities, and tolerance/response to therapy. Long acting pharmaceutical composi-tions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that human galectin-8 can be used as a therapeutic molecule to increase the immune response, e.g., when administered with vaccine preparations. It is further contemplated that antisense molecules capable of reducing the expression of human galectin-8 can be as therapeutic molecules to reduce the metastatic potential of neoplastic tissue. Still further it is contemplated that antibodies directed against human galectin-8 and capable of neutralizing the biological activity of human galectin-8 may be used as therapeutic molecules to reduce the metastatic potential of neoplastic tissues.

The examples below are provided to illustrate the subject invention and are not included for the purpose of limiting the invention.

EXAMPLES

I. HEARNOT01 cDNA Library Construction

The heart tissues for the HEARNOT01 cDNA library construction were obtained from a 56 year old Caucasian male and a 51 year-old Caucasian female (Lot#HAL194 and Lot#RU95-03-196, respectively; International Institute for the Advancement of Medicine, Exton Pa.). Each atrial or ventricular sample was individually was flash frozen, ground in a mortar and pestle. Tissue was lysed immediately in buffer containing guanidinium isothiocyanate and spun through cesium chloride. The precipitate was treated by several phenol chloroform extractions and ethanol precipitation at pH 8. Each of the samples was treated DNAse, and the polyadenylated mRNA was isolated and purified using OLIGOTEX (Qiagen Inc, Chatsworth Calif.).

First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDAZAD vector system (Stratagene); and the vector containing the pBLUESCRIPT phagemid (Stratagene) was transformed into *E. coli* host cells strain XL1-BLUEMRF (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which contained the gene for β-lactamase allowed transformed bacteria to grow on medium containing ampicillin.

II. Isolation And Sequencing Of cDNA Clones

Plasmid DNA was released from the cells and purified using the Miniprep Kit (Catalogue# 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS DNA purification system (Catalogue #A7100, Promega, Madison Wis.) or QIAWELL 8 Plasmid, QIAWELL PLUS DNA and QIAWELL ULTRA DNA purification systems (Qiagen, Chatsworth Calif.).

The cDNAs were sequenced by the method of Sanger F. and A. R. Coulson (1975; J Mol Biol 94:441f), using a Hamilton MICROLAB 2200 (Hamilton, Reno Nev.) in combination with four Peltier thermal cyclers (PTC200 from M. J. Research, Watertown Mass.) and Applied Biosystems 377 or 373 DNA sequencing systems (Perkin Elmer), and the reading frame was determined.

III. Homology Searching Of cDNA Clones And Their Deduced Proteins

Each cDNA was compared to sequences in GenBank using a search algorithm developed by Applied Biosystems and incorporated into the INHERIT 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al. (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA and protein sequences corresponding to the human galectin-8 gene (LGALS8) or protein with known nucleotide and protein sequences in GenBank revealed that the full-length human galectin-8 cDNA and protein sequences (i.e., SEQ ID NOS:1 and 2) were unique (i.e., not previously identified). Thus, SEQ ID NO:1 represents the first identified human galectin-8 homolog. This search revealed that the human galectin-8 protein shared some homology with the rat galectin-8 protein (see alignment in FIG. 2); more limited homology with nucleotide sequences encoding the rat galectin-8 protein (Accession number: U09824; NID: g71703 1) was found.

Short stretches of partial homology between the human galectin-8 protein sequence and the following protein sequences were identified (numbers refer to the owl27 database): pig lectin L-36 (A55664); rat galectin-4 [LEG4_RAT; Oda Y. et al. (1993), supra]; rat galectin-5 (A55932); pig SSC9G10 (SSC9G10); C. elegans CEZK892 (CEZK8923); and C. elegans 32 kD β-galactoside-binding lectin [LE32_CAEEL; Harabayashi J. (1992) J. Biochem. 111:553–55].

A number of expressed sequence tags (ESTs) present in Genbank databases were found to share short stretches of homology with SEQ ID NO:2. The largest stretch with the highest degree of homolog was between SEQ ID NO:2 and an EST from the gb95merck database (ie., GenBank 95 WashU-Merck ESTs); g900694 from the Merck database shared 254/259 bases with SEQ ID NO:2. The following ESTs listed in the Merck database contained shorter stretches of homology with SEQ ID NO:2: g1110080; g982968; and g727027. In addition, clone hmd3f11m5, a partial cDNA clone isolated from a HepG2 (a human liver cancer cell line) library was found to share 178/180 bases with SEQ ID NO:2 [database: gb95pri; accession no.: D17044; NID: g598773; Matoba R. (1994) Gene 146:199–207].

IV. Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul S. F. 1993 and 1990, supra) are used to search for identical or related molecules in nucleotide databases such as GenBank or the LIFESEQ™ database (Incyte, Palo Alto Calif.) (this technique is termed an "electronic northern"). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding human galectin-8 occurs. Abundance and percentage abundance are also reported. Abundance directly reflects the number of times a particular transcript is represented in a cDNA library, and percent abundance is abundance divided by the total number of sequences examined in the cDNA library.

Electronic northern analysis (FIG. 3) revealed that mRNA encoding human galectin-8 (SEQ ID NO:1) was present in libraries generated from the following tissues: heart (Incyte library: HEARNOT01); macrophages (adherent peripheral blood mononuclear cells) from a MLR (Incyte library: MMLR1DT01); lymphocytes (non-adherent peripheral blood mononuclear cells) from a MLR (Incyte library: TMLR3DT01); and fetal lung (Incyte library: LUNGFET03). This analysis revealed that human galectin-8 transcripts were most abundant in adult heart among the tissues examined. In addition, this analysis revealed that expression of human galectin-8 transcripts was more abundant in adult as compared to fetal tissues. This finding is consistent with the report that rat galectin-8 is expressed at very low levels in fetal tissues (i.e., whole rat embryos; Hadari Y. R. et al., supra). Thus, expression of human, as well as, rat galectin-8 appears to be developmentally regulated.

V. Extension Of The Sequence Encoding Human Galectin-8

The nucleic acid sequence of SEQ ID NO:2 is used to design oligo-nucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the know sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO primer analysis software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M. J. Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J. et al., supra). After incubation for one hour at 37° C., the whole transformation mixture is plated on Luria Bertani (LB)-agar (Sambrook J. et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3x) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI. Labeling And Use Of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN, Boston Mass.). The labeled oligonucleotides are substantially purified with SEPHADEX G-25 super fine resin column (Pharmacia). A portion containing $10^7$ counts per minute of each of the sense and antisense oligonucleotides is used in a typical membrane based hybridization analysis of human genomic DNA digested with one of the following endonucleases (AseI, BglII, EcoRI, PstI, XbaI, or PvuII; DuPont NEN).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×x saline sodium citrate and 0.5% sodium dodecyl sulfate. After XOMAT AR film (Kodak, Rochester N.Y.) is exposed to the blots, or the blots are exposed to a Phosphoimager cassette (Molecular Dynamics, Sunnyvale Calif.), hybridization patterns are compared visually.

VII. Antisense Molecules

The sequence encoding human galectin-8, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to the coding sequence of human galectin-8 as shown in FIGS. 1A and 1B is used to inhibit expression of naturally occurring sequence. The complementary oligonucleotide is designed from the most unique 5' sequence as shown in FIGS. 1A and 1B and used either to inhibit transcription by preventing promoter binding to the upstream nontranslated sequence or translation of an human galectin-8-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII. Expression Of Human Galectin-8

Expression of the human galectin-8 is accomplished by subcloning the cDNAs into appropriate vectors and transfecting the vectors into host cells. In this case, the cloning vector, PBLUESCRIPT, previously used for the generation of the cDNA library is used to express human galectin-8 in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a polylinker containing a number of unique restriction sites.

Induction of an isolated, transfected bacterial strain with IPTG using standard methods produces a fusion protein which consists of the first seven residues of β-galactosidase, about 5 to 15 residues of linker, and the full length human galectin-8. The signal sequence directs the secretion of human galectin-8 into the bacterial growth media which can be used directly in the following assay for activity.

In addition, the human galectin-8 protein may be expressed as a fusion protein containing a histidine tag or GST tag using commercially available expression vectors [e.g., QIAexpress vectors (Qiagen) and pGex vectors (Pharmacia), respectively]. Suitable host cells and conditions for the induction/expression of the desired expression vectors are known to the art and available commercially. Histidine tagged human galectin-8 may be purified from E. coli extracts using metal chelation chromatography using commercially available resins [e.g., Ni-NTA Agarose (Qiagen)]. GST-tagged human galectin-8 may be purified from E. coli extracts using affinity chromatography using commercially available resins [e.g., glutathione-Sepharose beads (Pharmacia)]. Several other expression systems are available and may be employed to express fusion proteins comprising human galectin-8 (e.g., pMAL vectors from New England Biolabs, Beverly, Mass.).

IX. Assay For Human Galectin-8 Biological Activity

The ability of human galectin-8 synthesized as described above to bind to β-galactoside sugars is examined as follows. The human galectin-8 fusion protein is applied to a lactosyl-SEPHAROSE column, and the column is eluted with 0.1M lactose. The presence of a protein having the size expected for the human galectin-8 fusion protein in the elute indicates the ability of the recombinant human galectin-8 protein to bind β-galactoside sugars. Alternative methods for accessing the ability of the recombinant human galectin-8 protein to bind lactose are known to the art (see, for example, the binding of recombinant galectins with immobolized asialofeutin in the presence or absence of 150 mM lactose described by Madsen P. et al., supra).

Another biological activity of the recombinant human galectin-8, the ability to agglutinate cells is demonstrated using the assay described by Hadari Y. R. et al, supra. Briefly, trypsin-treated rabbit erythrocytes are prepared by incubation of rabbit erythrocytes with 0.1% trypsin [in phosphate buffered saline (PBS)] hour at 37° C.; the cells are then washed five times in 10 volumes of 0.9% sodium chloride per ml of packed cells. The cells are reuspended in 0.9% sodium chloride to produce a suspension of cells having an absorbance of 1.5 at 620 nm. One-half of a milliliter (0.5 mL) of this suspension is incubated for 45 minutes at room temperature with 0.1 to 5 μg/ml recombinant human galectin-8. Aliquots (0.2 ml) of the upper part of the solution are removed and mixed with 0.8 ml of PBS and the optical density at 620 nm is examined.

The overexpression of a number of galectins have been implicated in the metastatic potential of cells. The ability of human galectin-8 to promote metastasis is examined by overexpressing human galectin-8 in a weakly metastatic fibrosarcoma cell line (e.g., UV-2237-cl-15 fibroscarcoma cells) and examining whether metastatic potential is increased using the assay described by Raz A. et al. [(1990), supra]. Vectors expressing the nucleic acid sequence or purified human galectin-8 can be delivered to the cells using technologies well known in the art. If overexpression of human galectin-8 correlates with an increase in metastatic potential, a reduction in the expression of human galectin-8 in metastatic or pre-metastatic tissues should be therapeutic. Antisense galectin-8 molecules (described in Example VII) or anti-human galectin-8 antibodies (described in Example X below) may be administered to tumor tissue in a patient to reduce metastases.

As discussed in Example IV above, human galectin-8 is expressed in both macrophages and lymphocytes isolated from MLRs. This suggests that human galectin-8 may be used as an indication of the presence of inflamatory responses, including GVH responses. The expression of galectin-8 may be used to follow the presence of an inflammatory response in patient tissues before, during and after treatment with pharmaceutical compounds administered to suppress the immune response. Biopsied cells from a patient before and after treatment may be examined for the expression of human galectin-8 (mRNA or protein); a reduction in human galectin-8 expression should correlate with a reduction in the immune or inflamatory response.

X. Production Of Human Galectin-8 Specific Antibodies

Human galectin-8 substantially purified using polyacrylamide gel electrophoresis (PAGE) (Sambrook, supra) is used to immunize suitable animals (e.g., rabbits, hamsters, rats, mice, goats, sheep, etc.) and to produce antibodies using standard protocols (alternatively, recombinant human galectin-8 fusion proteins may be purified by affinity or metal chelation chromatography and used to immunize animals). The amino acid sequence translated from human galectin-8 is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F. M. et al. (supra).

Typically, the oligopeptides are 15 residues in length, synthesized using an Applied Biosystems 43/A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel F. M. et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Purified human galectin-8 (native or fusion proteins) may be used to generate antibodies which react specifically with the human galectin-8 protein. The production of both polyclonal and monoclonal antibodies utilize techniques standard to the art. Polyclonal antibodies contain a mixture of different types of antibodies that are specific for many different antigens present on the immunogen. Monoclonal antibodies contain a single species of antibody having a defined specificity.

Briefly, polyclonal antibodies are generated by immunization of a host animal with a purified protein. The serum of the immunized animal will contain antibodies directed against one or more epitopes of the injected protein. When rabbits are used for the production of polyclonal antibodies specific for human galectin-8, 50 to 1000 µg of purified human galectin-8 is mixed with complete Freund's adjuvant and administered subcutaneously (s.c.) to the rabbit. Typically, multiple s.c. injections, each containing a maximum volume of about 400 µl are administered (up to 10 injections may be performed per animal). Alternatively, the immunogen may administered by intramuscular or intradermal injection. Four to six weeks following the initial or primary injection, secondary or booster injections are administered (these may utilize incomplete Freund's adjuvant). Additional boosts are given in 4–6 week intervals following the last injection. Immunized rabbits are bled (e.g., using the marginal ear vein) and the serum is screened for the presence of antibodies which react specifically with human galectin-8 (e.g., by ELISA screening).

Immunization of mice is conducted as described above with the exception that the dose of antigen is 10–50 µg per injection (250 µl antigen solution mixed with 250 µl complete Freund's adjuvant) and injection is given intraperitoneally (i.p.). The first boost is given two weeks later and employs incomplete Freund's adjuvant; subsequent boosts are given at about 3 week intervals. Serum is collected from the immunized mice (e.g., by tail bleeding) and is screened for the presence of antibodies which react specifically with human galectin-8 (e.g., by ELISA screening).

Monoclonal antibodies are produced by immunizing a host animal with purified human galectin-8 protein (native or fusion). Once the host has produced antibodies specific for human galectin-8 protein, the spleen of the host is removed. The plasma cells present in the spleen of the immune host are then fused with a myeloma cell (the "fusion partner") to produce hybridoma cells. When mice are immunized for the production of plasma cells to be used to generate hybridomas, suitable fusion partners include the X63Ag8.653, Sp2/0-Ag14, FO, NSI/1-Ag4-1, NSO/1 and FOX-NY cell lines [Antibodies: A Laboratory Manual, Harlow and Lane, Eds. (1988) Cold Spring Harbor Laboratory Press, Cold Spring Harbor, N.Y., p. 144]. When rats are immunized for the production of plasma cells to be used to generate hybridomas, suitable fusion partners include the YB2/0 and IR983F cell lines (Harlow and Lane, supra). Mice or rats are immunized as described above. Following the generation of specific anti-human galectin-8 antibodies in the animals (typically following 2 to 3 booster injection and about 56 days following the initial injection), spleens are removed and splenocytes are fused (e.g., using polyethylene glycol) with the desired fusion partner. The fused cells are diluted in the appropriate selective medium and plated in multiwell culture plates. Each hybridoma cell produces a single type of antibody. Culture supernatant from individual hybridoma cells (removed from the hybridomas about 1 week following plating) is screened using standard techniques to identify those hybridoma cells expressing monoclonal antibodies reactive with human galectin-8 (see Harlow and Lane, supra for a review of screening techniques).

When a fusion protein is utilized for the production of antibodies, the resulting antibodies may contain antibodies directed against the fusion partner (e.g., GST). These anti-fusion partner antibodies may be removed from a polyclonal sera by chromatography of the sera on a column containing the fusion partner immobilized to a solid support such as Sepharose beads (Pharmacia). For example, to remove anti-GST antibodies from a polyclonal sera raised against a GST fusion protein, the sera is chromatographed on a resin comprising the GST protein covalently linked to glutathione Sepharose. Anti-fusion partner antibodies may be excluded during the routine screening of hybridomas during the production of monoclonal antibodies.

XI. Purification Human Galectin-8 Using Specific Antibodies

Naturally occurring or recombinant human galectin-8 is substantially purified by immunoaffinity chromatography using antibodies specific for human galectin-8. An immunoaffinity column is constructed by covalently coupling human galectin-8 antibody to an activated chromatographic resin such as CnBr-activated SEPHAROSE (Pharmacia Biotech). After the coupling, the resin is blocked and washed according to the manufacturer's instructions.

Cytosolic fractions from cells expressing human galectin-8 are prepared by methods well known in the art (i.e., homogenization of cells or tissue followed by centrifugation of the homogenate at 100,000×g for 1 hour at 4° C.

as described by Hadari Y. R. et al., supra). Alternatively, a recombinant human galectin-8 fragment containing an appropriate signal sequence may be secreted in useful quantity into the medium in which transfected cells are grown.

A human galectin-8-containing preparation is passed over the immunoaffinity column, and the column is washed under conditions that allow the preferential absorbance of human galectin-8 (e.g., high ionic strength buffers in the presence of detergent). The column is eluted under conditions that disrupt antibody/human galectin-8 binding (e.g., a buffer of pH 2–3 or a high concentration of a chaotrope such as urea or thiocyanate ion), and human galectin-8 is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated polynucleotide encoding human galectin-8 which hybridizes under stringent conditions of 5× SSPE, 0.5% SDS, 5× Denhardt's reagent, and 100 μg/ml denatured salmon sperm to the isolated polynucleotide encoding a polypeptide comprising the amino acid sequence of SEQ ID NO: 1.

2. An isolated polynucleotide encoding a polypeptide comprising the amino acid sequence of SEQ ID NO:1.

3. An expression vector comprising the polynucleotide sequence of claim 2.

4. A host cell comprising the expression vector of claim 3.

5. A method for producing a polypeptide comprising the amino acid sequence of SEQ ID NO:1, the method comprising the steps of:

a) culturing the host cell of claim 4 under conditions suitable for the expression of the polypeptide; and
b) recovering the polypeptide from the host cell culture.

6. An isolated polynucleotide which is completely complementary to the polynucleotide of claim 2.

7. A method for detecting the presence of a polynucleotide encoding a polypeptide comprising the amino acid sequence of SEQ ID NO:1 in a biological sample containing nucleic acid, the method comprising the steps of:

a) hybridizing the polynucleotide of claim 6 to the nucleic acid of the biological sample, thereby forming a hybridization complex; and
b) detecting the hybridization complex, wherein the presence of the hybridization complex correlates with the presence of the polypeptide in the biological sample.

8. The method of claim 7 wherein the detecting occurs under conditions that permit the detection of alterations in the polynucleotide of SEQ ID NO:2 in the biological sample.

9. An isolated polynucleotide comprising the nucleic acid sequence of SEQ ID NO:2.

10. An antisense molecule comprising the nucleic acid sequence complementary to the polynucleotide of claim 9.

11. A pharmaceutical composition comprising the antisense molecule of claim 10 and a pharmaceutically acceptable excipient.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 264 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: HEARNOT01
        ( B ) CLONE: 305603

( x i ) SEQUENCE DESCRIPTION: SEQ ID NO:1:

```
Met Met Leu Ser Leu Asn Asn Leu Gln Asn Ile Ile Tyr Asn Pro Val
 1               5                  10                  15

Ile Pro Tyr Val Gly Thr Ile Pro Asp Gln Leu Asp Pro Gly Thr Leu
             20                  25                  30

Ile Val Ile Cys Gly His Val Pro Ser Asp Ala Asp Arg Phe Gln Val
             35                  40                  45

Asp Leu Gln Asn Gly Ser Ser Val Lys Pro Arg Ala Asp Val Ala Phe
         50                  55                  60

His Phe Asn Pro Arg Phe Lys Arg Ala Gly Cys Ile Val Cys Asn Thr
 65                  70                  75                  80

Leu Ile Asn Glu Lys Trp Gly Arg Glu Glu Ile Thr Tyr Asp Thr Pro
                 85                  90                  95

Phe Lys Arg Arg Lys Ser Phe Glu Ile Val Ile Met Val Leu Lys Asp
             100                 105                 110

Lys Phe Gln Asp Leu Gln Ser Thr Gln Ala Ser Ser Leu Glu Leu Thr
         115                 120                 125

Glu Ile Ser Arg Glu Asn Val Pro Lys Ser Gly Thr Xaa Gln Leu Cys
     130                 135                 140

Leu Pro Phe Xaa Ala Arg Leu Asn Thr Pro Met Gly Pro Gly Arg Thr
145                 150                 155                 160

Val Val Val Lys Gly Glu Val Asn Ala Asn Ala Lys Ser Phe Asn Val
                 165                 170                 175

Asp Leu Leu Ala Gly Lys Ser Lys Asp Ile Ala Leu His Leu Asn Pro
             180                 185                 190

Arg Leu Asn Ile Lys Ala Phe Val Arg Asn Ser Phe Leu Gln Glu Ser
         195                 200                 205

Trp Gly Glu Glu Glu Arg Asn Ile Thr Ser Phe Pro Phe Ser Pro Gly
```

```
            210                      215                      220
Met  Tyr  Phe  Glu  Met  Ile  Ile  Tyr  Cys  Asp  Val  Arg  Glu  Phe  Lys  Val
225                      230                      235                      240

Ala  Val  Asn  Gly  Val  His  Ser  Leu  Glu  Tyr  Lys  His  Arg  Phe  Lys  Glu
                    245                      250                      255

Leu  Xaa  Ser  Ile  Ser  Ala  Xaa  Asn
               260
```

( 2 ) INFORMATION FOR SEQ ID NO:2:

( i ) SEQUENCE CHARACTERISTICS:
        ( A ) LENGTH: 1078 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: HEARNOT01
        ( B ) CLONE: 305603

( x i ) SEQUENCE DESCRIPTION: SEQ ID NO:2:

```
TCCCAGGTTC  AAGCAATTGT  CCTGTCTCAG  CCTCCTGAGT  AGCTGGGACT  ACAGGGCCAG     60

TGCCTCAGTT  TCAATCCAGG  TAACCTTTAA  ATGAAACTTG  CCTAAAATCT  TAGGTCATAC    120

ACAGAAGAGA  CTCCAATCGA  CAAGAAGCTG  GAAAAGAATG  ATGTTGTCCT  TAAACAACCT    180

ACAGAATATC  ATCTATAACC  CGGTAATCCC  GTATGTTGGC  ACCATTCCCG  ATCAGCTGGA    240

TCCTGGAACT  TTGATTGTGA  TATGTGGGCA  TGTTCCTAGT  GACGCAGACA  GATTCCAGGT    300

GGATCTGCAG  AATGGCAGCA  GTGTGAAACC  TCGAGCCGAT  GTGGCCTTTC  ATTTCAACCC    360

TCGTTTCAAA  AGGGCCGGCT  GCATTGTTTG  CAATACTTTG  ATAAATGAAA  AATGGGGACG    420

GGAAGAGATC  ACCTATGACA  CGCCTTTCAA  AAGAAGAAAA  TCTTTTGAGA  TCGTGATTAT    480

GGTGCTAAAG  GACAAATTCC  AGGACTTACA  AAGTACCCAA  GCATCTAGTC  TGGAACTGAC    540

AGAGATAAGT  AGAGAAAATG  TTCCAAAGTC  TGGCACGNCC  CAGCTTTGCC  TGCCATTCGN    600

TGCAAGGTTG  AACACCCCCA  TGGGCCCTGG  ACGAACTGTC  GTCGTTAAAG  GAGAAGTGAA    660

TGCAAATGCC  AAAAGCTTTA  ATGTTGACCT  ACTAGCAGGA  AAATCAAAGG  ATATTGCTCT    720

ACACTTGAAC  CCACGCCTGA  ATATTAAAGC  ATTTGTAAGA  AATTCTTTTC  TTCAGGAGTC    780

CTGGGGAGAA  GAAGAGAGAA  ATATTACCTC  TTTCCCATTT  AGTCCTGGGA  TGTACTTTGA    840

GATGATAATT  TACTGTGATG  TTAGAGAATT  CAAGGTTGCA  GTAAATGGCG  TACACAGCCT    900

GGAGTACAAA  CACAGATTTA  AAGAGCTCAR  CAGTATTTCA  GCTGNAAATT  AATGNGNCCA    960

NCCNATTNCT  GAGAATANAG  ACNTTNGACC  TNCNTCACAG  AAGTTNTCAN  AAAACCNAAA   1020

AATGGAAGGT  CTTTGTGNTA  ANAGTTCCGT  TGNTTANAAN  CTCTCATCTT  ANTTTATT    1078
```

( 2 ) INFORMATION FOR SEQ ID NO:3:

( i ) SEQUENCE CHARACTERISTICS:
        ( A ) LENGTH: 316 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 717032

( x i ) SEQUENCE DESCRIPTION: SEQ ID NO:3:

-continued

| | | | | | | | | | | | | | | | |
|---|---|---|---|---|---|---|---|---|---|---|---|---|---|---|---|
| Met 1 | Leu | Ser | Leu | Ser 5 | Asn | Leu | Gln | Asn | Ile 10 | Ile | Tyr | Asn | Pro | Thr 15 | Ile |
| Pro | Tyr | Val | Ser 20 | Thr | Ile | Thr | Glu | Gln 25 | Leu | Lys | Pro | Gly | Ser 30 | Leu | Ile |
| Val | Ile | Arg 35 | Gly | His | Val | Pro | Lys 40 | Asp | Ser | Glu | Arg | Phe 45 | Gln | Val | Asp |
| Phe | Gln 50 | His | Gly | Asn | Ser | Leu 55 | Lys | Pro | Arg | Ala | Asp 60 | Val | Ala | Phe | His |
| Phe 65 | Asn | Pro | Arg | Phe | Lys 70 | Arg | Ser | Asn | Cys | Ile 75 | Val | Cys | Asn | Thr | Leu 80 |
| Thr | Asn | Glu | Lys | Trp 85 | Gly | Trp | Glu | Glu | Ile 90 | Thr | His | Asp | Met | Pro 95 | Phe |
| Arg | Lys | Glu | Lys 100 | Ser | Phe | Glu | Ile | Val 105 | Ile | Met | Val | Leu | Lys 110 | Asn | Lys |
| Phe | His | Val 115 | Ala | Val | Asn | Gly | Lys 120 | His | Ile | Leu | Leu | Tyr 125 | Ala | His | Arg |
| Ile | Asn 130 | Pro | Glu | Lys | Ile | Asp 135 | Thr | Leu | Gly | Ile | Phe 140 | Gly | Lys | Val | Asn |
| Ile 145 | His | Ser | Ile | Gly | Phe 150 | Arg | Phe | Ser | Ser | Asp 155 | Leu | Gln | Ser | Met | Glu 160 |
| Thr | Ser | Thr | Leu | Gly 165 | Leu | Thr | Gln | Ile | Ser 170 | Lys | Glu | Asn | Ile | Gln 175 | Lys |
| Ser | Gly | Lys | Leu 180 | His | Leu | Ser | Leu | Pro 185 | Phe | Glu | Ala | Arg | Leu 190 | Asn | Ala |
| Ser | Met | Gly 195 | Pro | Gly | Arg | Thr | Val 200 | Val | Val | Lys | Gly | Glu 205 | Val | Asn | Thr |
| Asn | Ala 210 | Thr | Ser | Phe | Asn | Val 215 | Asp | Leu | Val | Ala | Gly 220 | Arg | Ser | Arg | Asp |
| Ile 225 | Ala | Leu | His | Leu | Asn 230 | Pro | Arg | Leu | Asn | Val 235 | Lys | Ala | Phe | Val | Arg 240 |
| Asn | Ser | Phe | Leu | Gln 245 | Asp | Ala | Trp | Gly | Glu 250 | Glu | Glu | Arg | Asn | Ile 255 | Thr |
| Cys | Phe | Pro | Phe 260 | Ser | Ser | Gly | Met | Tyr 265 | Phe | Glu | Met | Ile | Ile 270 | Tyr | Cys |
| Asp | Val | Arg 275 | Glu | Phe | Lys | Val | Ala 280 | Val | Asn | Gly | Val | His 285 | Ser | Leu | Glu |
| Tyr | Lys 290 | His | Arg | Phe | Lys | Asp 295 | Leu | Ser | Ser | Ile | Asp 300 | Thr | Leu | Ala | Val |
| Asp 305 | Gly | Asp | Ile | Arg | Leu 310 | Leu | Asp | Val | Arg | Ser 315 | Trp | | | | |